United States Patent [19]

Long et al.

[11] Patent Number: Plant 6,279

[45] Date of Patent: Sep. 6, 1988

[54] KENTUCKY BLUEGRASS

[75] Inventors: John A. Long; Virgil D. Meier; Eugene W. Mayer, all of Marysville, Ohio

[73] Assignee: The O.M. Scott & Sons Company, Marysville, Ohio

[21] Appl. No.: 872,537

[22] Filed: Jun. 10, 1986

[51] Int. Cl.[4] ..... A01H 5/00

[52] U.S. Cl. ..... Plt./88

[58] Field of Search ..... Plt. 88

*Primary Examiner*—Robert E. Bagwill

*Attorney, Agent, or Firm*—James B. Raden

[57] ABSTRACT

A variety of Kentucky bluegrass having a good level of disease resistance, excellent turf performance and excellent seed yield.

1 Drawing Sheet

BACKGROUND

Kentucky bluegrasses have been disclosed in U.S. Plant Pat. No. 3,156 which issued on May 9, 1972; U.S. Plant Pat. No. 3,186 which issued on May 23, 1972 and U.S. Plant Pat. No. 4,336 which issued on Nov. 28, 1978.

SUMMARY OF THE VARIETY

The present invention relates to a new and distinct variety of *Poa pratensis* which has been designated Ba 61-91 Kentucky bluegrass.

Ba 61-91 plant material originated as one of several spaced plants at Marysville, Ohio and seed of Ba61-91 was produced first at Marysville, Ohio, then Salem and Gervais, Oreg. This seed was used to plant turf for performance evaluation trials.

Ba 61-91 Kentucky bluegrass reproduces asexually both apomictically and vegetatively; i.e., by tillers and rhizomes. All asexually reproduced Ba 61-91 offspring appear to show complete conformity with the mother plant.

Ba 61-91 has a number of highly desirable characteristics including a good level of resistance to Helminthosporium spp., *Ustilago striiformis, Fusarium roseum, Sclerotinia homoeocarpa, Puccinia graminis,* Corticium spp., Rhizoctonia spp., and Pythium spp. It has a desirable dark green color and produces a good, dense turf that persists over a wide range of environmental conditions.

DETAILED DESCRIPTION OF THE VARIETY

Figure 1:
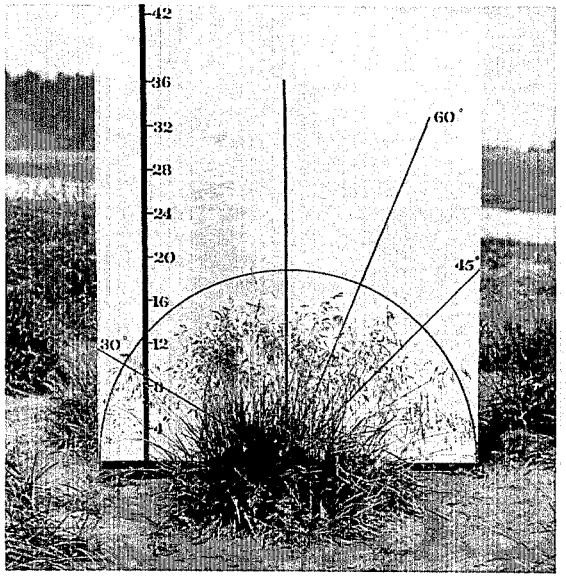
FIG. 1 is a photograph of Ba 61-91 Kentucky bluegrass plant after anthesis at Gervais, Oreg.
Figure 2:
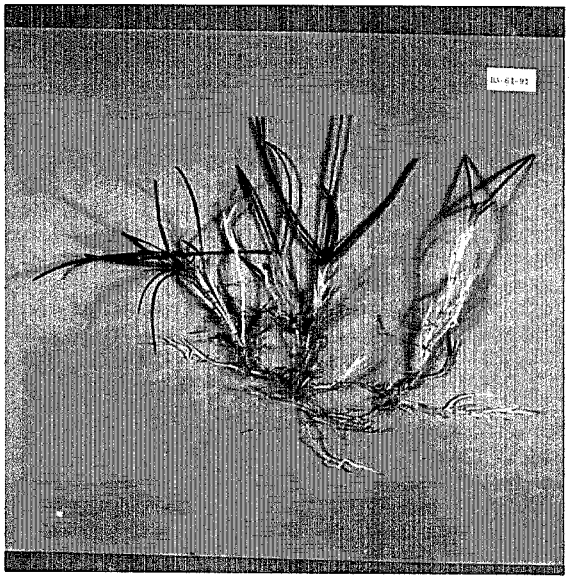
FIG. 2 is a photograph of Ba 61-91 Kentucky bluegrass plant in the vegetative stage including the extensive root and rhizome system.
Figure 3:
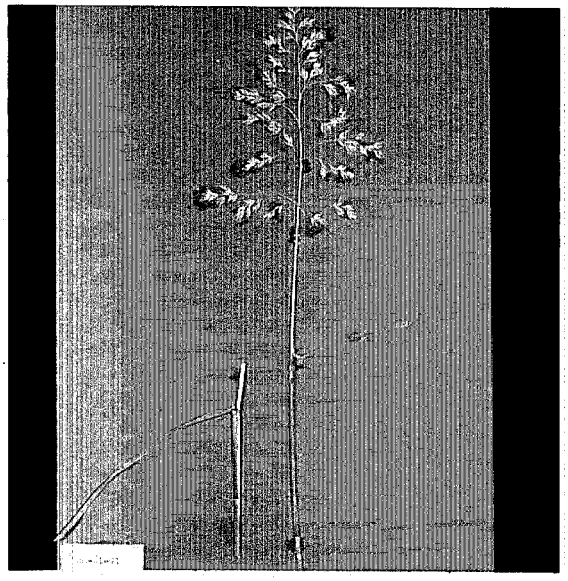
FIG. 3 is a photograph of Ba 61-91 Kentucky bluegrass panicle.
Figure 4:
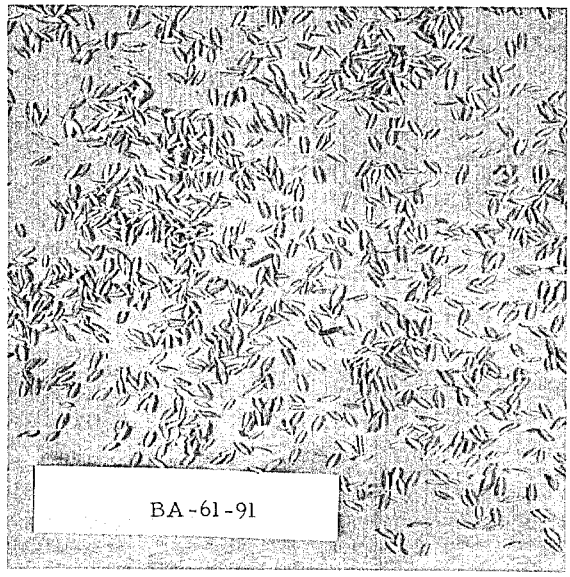
FIG. 4 is a photograph of Ba 61-91 Kentucky bluegrass seed.

The morphological characteristics of Ba 61-91 and other commercially available bluegrass varieties are compared in Table 1.

TABLE 1

Morphological comparison of Ba 61-91 and other bluegrass varieties at Gervals, Oregon

| Variety | Floret Length (mm) | Spikelet Length (mm) | Glume Length (mm) Glume 1 | Glume Length (mm) Glume 2 | Mature Plant Height (cm) |
|---|---|---|---|---|---|
| Ba 61-91 | 3.95 | 5.52 | 2.87 | 3.13 | 46.5 |
| Baron | 3.17 | 4.16 | 2.55 | 2.90 | 60.7 |
| Merion | 2.72 | 4.56 | 2.51 | 2.76 | 62.7 |
| Merit | 3.43 | 4.73 | 2.67 | 3.02 | 72.0 |
| Newport | 3.46 | 5.42 | 3.21 | 3.60 | 73.8 |
| Victa | 3.30 | 4.48 | 2.72 | 3.05 | 64.0 |
| LSD(.05) | 0.35 | 0.17 | 0.11 | 0.10 | 7.9 |

| Variety | No. of Whorls per Panicle | Panicle Length (cm) | Peduncle Length (cm) | Flagleaf Length (cm) | Flagleaf Width (mm) |
|---|---|---|---|---|---|
| Ba 61-91 | 10.0 | 6.9 | 35.8 | 3.4 | 3.6 |
| Baron | 11.3 | 8:4 | 32.7 | 5.3 | 3.5 |
| Merion | 11.3 | 9.6 | 40.4 | 6.5 | 4.7 |
| Merit | 11.0 | 5.8 | 38.1 | 6.0 | 3.8 |
| Newport | 13.0 | 10.3 | 37.9 | 6.3 | 4.3 |
| Victa | 13.0 | 8.9 | 40.4 | 6.7 | 4.9 |
| LSD(.05) | 1.3 | 3.6 | 7.3 | 2.3 | 0.9 |

| Variety | No. of Branches Lowest Whorl | No. of Branches Third Whorl | No. of Florets per Spikelet |
|---|---|---|---|
| Ba 61-91 | 4.5 | 3.0 | 4.3 |
| Baron | 5.0 | 4.3 | 2.8 |
| Merion | 3.7 | 2.7 | 4.7 |
| Merit | 6.0 | 4.0 | 3.2 |
| Newport | 4.3 | 4.0 | 4.6 |
| Victa | 4.7 | 4.7 | 3.0 |
| LSD(.05) | 0.7 | 1.2 | 0.7 |

As shown by the foregoing table, the morphological characteristics of Ba 61-91 afford a basis for distinguishing it from other varieties of *Poa pratensis* such as those listed in the table.

Mowed plots of Ba 61-91 have been evaluated under turf conditions in many different tests and at numerous locations. Turfgrass performance information presented indicates the distinctiveness of Ba 61-91 compared to other bluegrass varieties and its desirable characteristics which enable it to provide good performance as described below.

Disease resistance is a highly significant and desirable characteristic that is necessary to the maintenance of good quality turf. Ba 61-91 Kentucky bluegrass has been demonstrated to provide good resistance to many major types of turf diseases in varied geographical locations.

Comparisons of Ba 61-91 and other bluegrasses for resistance to red thread (Corticium spp.), Pythium blight (Pythium spp.), Fusarium blight (*Fusarium roseum*) which is also known as Fusarium patch, leaf spot (Helminthesporium spp) which is also known as melting out, and dollar spot (*Sclerotinia homoeocarpia*) diseases are presented in Table 2.

TABLE 2

Disease ratings of BA 61-91 and other bluegrass varieties. 1983.

| Variety | Red Thread Blacksburg, VA | Pythium blight Urbana, IL | Disease Ratings* Fusarium blight Stillwater, OK |
|---|---|---|---|
| Ba 61-91 | 6.7 | 9.0 | 8.3 |
| A-34 | 5.7 | 6.3 | 7.7 |
| Adelphi | 6.0 | 8.3 | 8.3 |
| America | 6.7 | 6.3 | 9.0 |
| Baron | 6.3 | 9.0 | 8.8 |
| Birka | 6.0 | 5.7 | 8.7 |
| Cheri | 5.7 | 7.7 | 9.0 |
| Eclipse | 7.7 | 9.0 | 9.0 |
| Enmundi | 6.0 | 7.7 | 8.0 |
| Fylking | 6.0 | 8.3 | 7.7 |
| Glade | 5.3 | 5.7 | 8.7 |
| Kenblue | 4.0 | 3.7 | 8.7 |
| Merion | 6.0 | 9.0 | 8.7 |
| Merit | 7.3 | 9.0 | 8.3 |
| Nassau | 6.7 | 8.0 | 8.3 |
| Parade | 6.3 | 8.7 | 8.3 |
| Ram I | 6.7 | 6.3 | 8.5 |
| S.D. Common | 4.3 | 4.3 | 9.0 |
| Sydsport | 5.7 | 7.0 | 7.7 |
| LSD (.05) | 1.5 | 1.6 | 1.7 |

| Variety | Disease Ratings* Fusarium patch Moscow, ID | Melting Out -Spring 3 Locations** | Dollar Spot 3 Loca-cations*** | Mean |
|---|---|---|---|---|
| Ba 61-91 | 8.0 | 6.4 | 6.8 | 7.53 |
| A-34 | 5.7 | 4.8 | 6.9 | 6.18 |
| Adelphi | 8.3 | 6.3 | 7.1 | 7.38 |
| America | 6.0 | 5.4 | 6.8 | 6.70 |
| Baron | 5.3 | 6.3 | 6.7 | 7.07 |
| Birka | 5.3 | 6.3 | 6.6 | 6.43 |
| Cheri | 6.0 | 5.8 | 5.9 | 6.68 |
| Eclipse | 6.3 | 7.2 | 7.7 | 7.82 |
| Enmundi | 5.3 | 5.8 | 7.1 | 6.65 |
| Fylking | 6.7 | 6.0 | 7.1 | 6.97 |
| Glade | 8.7 | 5.9 | 6.9 | 6.87 |
| Kenblue | 5.3 | 2.8 | 7.2 | 5.28 |
| Merion | 7.7 | 6.4 | 6.9 | 7.45 |
| Merit | 7.3 | 6.4 | 6.1 | 7.40 |
| Massau | 6.7 | 7.3 | 6.8 | 7.30 |
| Parade | 7.0 | 5.4 | 7.0 | 7.12 |
| Ram I | 7.0 | 5.5 | 6.6 | 6.77 |
| S.D. Common | 7.0 | 2.9 | 7.6 | 5.85 |
| Sydsport | 3.0 | 6.0 | 5.7 | 5.85 |
| LSD (.05) | 3.2 | 0.8 | 1.0 | |

*Rating Scale: 1-9, 9 = no disease
**North Brunswick, NJ; Beltsville, MD; Blacksburg, VA
***Newark, DE (irrigated and not irrigated); Urbana, IL With continued reference to the disease resistance of Ba 61-91, Table 3 provides further comparative data for Ba 61-91 and other bluegrasses showing the high level of resistance of Ba 61-91 to leaf spot diseases based on information collected at various locations in the United States and at different times of the year.

TABLE 3

Comparison of Helminthosporium leafspot resistance of Ba 61-91 and other bluegrass varieties.

| Variety | Leafspot Ratings* Spring 13** | Summer 6** | Fall 2** | Mean 21** |
|---|---|---|---|---|
| Ba 61-91 | 6.9 a-d | 7.1 a-e | 8.3 a | 7.0 a-d |
| Baron | 6.6 a-g | 6.7 1-g | 8.3 s | 6.7 a-g |
| Cheri | 6.7 a-e | 6.8 a-f | 8.7 a | 6.8 a-f |
| Fylking | 6.8 a-e | 6.4 a-h | 8.6 a | 6.9 a-d |
| Glade | 6.4 a-g | 6.8 a-f | 8.6 | 6.5 a-g |
| Kenblue | 5.3 h | 6.2 a-h | 8.3 a | 5.4 h |
| Merion | 6.9 a-e | 6.8 a-f | 8.1 a | 6.9 a-d |
| Merit | 6.6 a-g | 6.4 a-h | 8.6 a | 6.6 a-g |
| Parade | 6.8 a-e | 7.7 a | 8.8 a | 7.0 a-d |
| Park | 5.5 g-h | 6.4 a-h | 8.4 a | 5.5 h |
| Rugby | 6.6 a-g | 7.2 a-e | 8.7 | 6.7 a-g |
| Touchdown | 6.9 a-e | 5.8 e-i | 8.6 a | 6.8 a-f |

Means followed by the same letter are not significantly different according to Duncan's Multiple Range Test (probability = 0.05).
Locations reporting leafspot resistance: Mt. Carmel, CT; Beltsville, MD; Fairland, MD; and Blacksburg, VA.
*Ratings Scale: 1-9, 9 = no injury
**Number of readings Comparisons of Ba 61-91 and other bluegrasses for resistance to stripe smut caused by the fungus *Ustilago striiformis*, Fusarium blight caused by the fungus *Fusarium roseum*, stem rust caused by the fungus *Puccinia graminis*, red thread caused by the fungus Corticium spp. and brown batch caused by the fungus Rhizoctonia spp. are presented in tables 4, 5, 6, 7 and 8, respectively.

TABLE 4

Comparison of stripe smut resistance of Ba 61-91 and other bluegrass varieties.

| Variety | Stripe Smut Ratings* New Brunswick, NJ | Fairland, MD | Mean |
|---|---|---|---|
| Ba 61-91 | 8.3 | 6.3 | 7.3 a-h |
| Adelphi | 8.7 | 8.3 | 8.5 a-b |
| Baron | 6.0 | 5.3 | 5.7 h-j |
| Fylking | 7.7 | 6.0 | 6.8 b-i |
| Glade | 9.0 | 9.0 | 9.0 a |
| Kenblue | 8.0 | 9.0 | 8.5 a-b |
| Merion | 2.7 | 3.0 | 2.8 m |
| Parade | 6.3 | 6.0 | 6.2 f-i |
| Park | 8.7 | 9.0 | 8.8 a |
| Rugby | 5.7 | 5.0 | 5.3 i-k |
| Windsor | 3.0 | 6.0 | 4.5 j-l |

Means followed by the same letter are not significantly different according to Duncan's Multiple Range Test (probability = 0.05).
*Rating Scale: 1-9, 9 = no injury

TABLE 5

Comparison of fusarium blight resistance of Ba 61-91 and other bluegrass varieties.

| Variety | Fusarium Blight Ratings* Mt. Carmel, CT | New Brunswick, NJ | Wye Mills, MD | Belts-ville, MD | Mean |
|---|---|---|---|---|---|
| Ba 61-91 | 6.7 | 4.3 | 7.7 | 7.0 | 6.5 a-i |
| Adelphi | 8.0 | 9.0 | 6.3 | 8.5 | 8.1 a |
| Baron | 7.0 | 6.0 | 7.3 | 5.7 | 6.3 a-i |
| Delft | 7.3 | 3.7 | 4.0 | 7.5 | 6.0 d-j |
| Fylking | 8.7 | 3.7 | 4.0 | 7.2 | 6.3 a-j |
| Geronimo | 7.0 | 3.7 | 4.3 | 7.2 | 5.9 e-j |
| Glade | 6.3 | 7.0 | 4.3 | 6.0 | 5.9 f-j |
| Merion | 7.0 | 6.0 | 5.7 | 8.2 | 7.0 a-i |
| Nugget | 6.3 | 5.0 | 3.5 | 6.2 | 5.8 f-j |
| Sydsport | 6.5 | 8.3 | 4.0 | 8.0 | 6.5 a-i |
| Touchdown | 7.0 | 7.0 | 6.0 | 5.5 | 6.0 d-j |

TABLE 5-continued

Comparison of fusarium blight resistance of Ba 61-91 and other bluegrass varieties.

| Variety | Fusarium Blight Ratings* | | | | |
|---|---|---|---|---|---|
| | Mt. Carmel, CT | New Brunswick, NJ | Wye Mills, MD | Belts-ville, MD | Mean |
| Vantage | — | 7.3 | 8.3 | 8.5 | 8.0 a–b |

Means followed by the same letter are not significantly different according to Duncan's Multiple Range Test (probability = 0.05).
*Rating Scale: 1–9, 9 = no injury

TABLE 6

Comparison of stem rust resistance of Ba 61-91 and other bluegrass varieties at Adelphia, New Jersey.

| Variety | Stem Rust Ratings* | |
|---|---|---|
| Ba 61-91 | 7.1 | 5.2 |
| Adelphi | 6.9 | 7.1 |
| America | 6.9 | 7.4 |
| Baron | 7.0 | 6.4 |
| Birka | 5.6 | 3.5 |
| Bonnieblue | 7.0 | 5.4 |
| Bristol | 7.7 | 7.7 |
| Eclipse | 7.0 | 4.7 |
| Merion | 3.6 | 2.4 |
| Merit | 7.0 | 5.7 |
| Nassau | 7.0 | 6.8 |
| Ram I | 7.3 | 7.0 |
| Touchdown | 5.7 | 3.5 |
| Vantage | 5.9 | 6.2 |
| LSD 5% | 1.0 | 0.9 |

*Rating Scale: 9 = no disease, 0 = turf killed

TABLE 7

Comparison of red thread resistance of Ba 61-91 and other bluegrass varieties at Newport News, Virginia.

| Variety | Red Thread Ratings* |
|---|---|
| Ba 61-91 | 5.7 a–f |
| Adelphi | 7.3 a |
| Baron | 3.7 e–i |
| Bonnieblue | 6.3 a–d |
| Cheri | 5.0 a–g |
| Glade | 3.3 f–i |
| Kenblue | 2.7 h–i |
| Nugget | 4.0 d–i |
| Park | 4.0 d–i |
| Sydsport | 5.0 a–g |
| Touchdown | 5.7 a–f |

Means followed by the same letter are not significantly different according to Duncan's Multiple Range Test (probability = 0.05).
*Rating Scale: 1–9, 9 = no injury

TABLE 8

Comparison of rhizoctonia brown patch resistance of Ba 61-91 and other bluegrass varieties at West Lafayette, Indiana.

| Variety | Brown Patch Ratings** |
|---|---|
| Ba 61-91 | 9.2 |
| Adelphi | 8.2 |
| America | 6.0 |
| Baron | 6.8 |
| Birka | 7.2 |
| Bristol | 6.2 |
| Cheri | 7.3 |
| Columbia | 7.8 |
| Enmundi | 8.0 |
| Fylking | 3.2 |
| Kenblue | 8.8 |
| Merion | 9.2 |
| Merit | 9.0 |
| Parade | 7.5 |
| Scenic | 8.2 |
| Sydsport | 3.7 |

TABLE 8-continued

Comparison of rhizoctonia brown patch resistance of Ba 61-91 and other bluegrass varieties at West Lafayette, Indiana.

| Variety | Brown Patch Ratings** |
|---|---|
| Vantage | 8.0 |

*Rating Scale: 1–10, 10 = no damage

Drought tolerance is a characteristic that allows the plant to perform well and survive long periods of stress under hot, dry conditions. Ba 61-91 has demonstrated good levels of drought tolerance at various locations in the United States as will be seen from the tabulated comparative test results in Table 9.

TABLE 9

Comparison of drought tolerance of Ba 61-91 and other bluegrass varieties.

| Variety | Drought Tolerance Ratings* | | | | |
|---|---|---|---|---|---|
| | Belts-ville, MD | Wye Mills, MD | Burlingham, VT | Blacksburg, Va | Mean |
| Ba 61-91 | 4.3 | 6.0 | 5.5 | 3.7 | 4.8 a–c |
| Adelphi | 5.0 | 5.0 | 5.7 | 3.5 | 4.7 a–e |
| Baron | 5.7 | 5.7 | 4.2 | 3.5 | 4.4 a–j |
| Cheri | 3.7 | 4.7 | 5.5 | 3.7 | 4.4 a–j |
| Fylking | 4.3 | 2.0 | 4.0 | 2.8 | 3.3 j–o |
| Glade | 4.0 | 3.3 | 3.8 | 3.2 | 3.6 f–o |
| Merion | 4.3 | 6.0 | 6.3 | 4.2 | 5.2 a |
| Nugget | 3.3 | 2.7 | 3.3 | 3.5 | 3.3 k–o |
| Parade | 4.0 | 4.7 | 3.5 | 3.0 | 3.6 f–o |
| Park | 3.0 | 3.7 | 2.8 | 4.3 | 3.5 g–o |
| Sydsport | 4.3 | 4.3 | 5.2 | 3.5 | 4.3 a–k |
| Vantage | 5.7 | 6.7 | 5.7 | 3.8 | 5.2 a |

Means followed by the same letter are no significantly different according to Duncan's Multiple Range Test (p = 0.05).
*Rating Scale: 1–9, 9 = no injury The color of Ba 61-91 turf is a desirable dark green color and is shown in comparison to other varieties in Table 10.

TABLE 10

Comparison of turf color of Ba 61-91 and other bluegrass varieties.

| Variety | Turf Color Ratings* | | |
|---|---|---|---|
| | Fayetteville, AR (1) | Fayetteville, AR (2) | Flagstaff, AZ |
| Ba 61-91 | 6.7 | 8.0 | — |
| A-34 | 4.7 | 5.0 | 5.3 |
| Adelphi | 6.0 | 6.3 | 6.0 |
| Baron | 7.0 | 8.0 | 6.3 |
| Birka | 6.0 | 7.0 | 5.7 |
| Cheri | 6.3 | 7.7 | 7.3 |
| Eclipse | 6.0 | 6.7 | — |
| Enmundi | 7.7 | 7.7 | 6.7 |
| Fylking | 6.3 | 6.7 | 5.3 |
| Glade | 7.7 | 7.7 | 6.3 |
| Kenblue | 4.7 | 4.3 | 5.7 |
| Merion | 4.7 | 4.0 | 6.7 |
| Merit | 7.0 | 7.3 | 6.7 |
| Parade | 4.3 | 4.0 | 5.3 |
| Sydsport | 6.3 | 7.3 | 6.7 |
| LSD (.05) | 1.4 | 1.4 | 1.5 |

| Variety | Turf Color Ratings* | | |
|---|---|---|---|
| | Agassiz, British Columbia | Moscow, ID | Fairland, MD |
| Ba 61-91 | 6.5 | 6.0 | 8.7 |
| A-34 | 6.0 | 5.0 | 8.3 |
| Adelphi | 6.3 | 6.0 | 8.3 |
| Baron | 6.3 | 5.7 | 8.0 |
| Birka | 6.0 | 5.0 | 8.0 |
| Cheri | 6.0 | 5.7 | 8.0 |
| Eclipse | 6.3 | 5.7 | 8.3 |
| Enmundi | 6.3 | 6.0 | 8.0 |
| Fylking | 6.3 | 4.7 | 8.0 |
| Glade | 7.0 | 6.3 | 8.7 |

TABLE 10-continued

Comparison of turf color of Ba 61-91 and other bluegrass varieties.

| | | | |
|---|---|---|---|
| Kenblue | 6.0 | 3.7 | 8.0 |
| Merion | 5.7 | 5.0 | 8.0 |
| Merit | 6.7 | 6.7 | 8.0 |
| Parade | 6.0 | 5.3 | 8.0 |
| Sydsport | 5.7 | 5.7 | 8.3 |
| LSD (.05) | 0.8 | 1.2 | 0.6 |

| | Turf Color Ratings* | |
|---|---|---|
| Variety | Pullman, WA | Mean |
| Ba 61-91 | 8.0 | 7.4 |
| A-34 | 8.0 | 6.0 |
| Adelphi | 8.0 | 6.7 |
| Baron | 8.3 | 7.1 |
| Birka | 7.7 | 6.5 |
| Cheri | 8.7 | 7.1 |
| Eclipse | 8.3 | 6.9 |
| Enmundi | 8.0 | 7.2 |
| Fylking | 7.3 | 6.4 |
| Glade | 7.3 | 7.3 |
| Kenblue | 7.7 | 5.7 |
| Merion | 8.0 | 6.0 |
| Merit | 8.3 | 7.2 |
| Parade | 7.3 | 5.8 |
| Sydsport | 8.0 | 6.9 |
| LSD (.05) | 0.8 | 0.4 |

*Rating Scale: 1-9, 9 = dark green
(1) High fertility test
(2) Low fertility test The various turfgrass characteristics described above are all taken into account in determining a turf quality rating. Great significance is attached to this rating because it is indicative of the general appearance, uniformity, and aesthetic value of a turf. Also, as all of the performance characteristics of the grass are taken into consideration, a good turf quality rating is an indication that the grass is free of disease and has good color, density and an acceptable texture. The turf quality ratings of Ba 61-91 from various times and locations in the United States are shown in Tables 11, 12 and 13 in comparison to several other varieties. Ba 61-91 produces a high quality turf at numerous locations in the United States. This, along with its high resistance to the major turf diseases as noted above, demonstrates the broad genetic adaptability of this grass.

TABLE 11

Turf quality of Ba 61-91 and other bluegrass varieties.

| | | Turf Quality Ratings* | | | |
|---|---|---|---|---|---|
| Variety | Agassiz, B.C. | Experiment, GA | Mississippi state, MS | Mead, NE | North Brunswick, NJ |
| Ba 61-91 | 5.9 | 5.2 | 4.9 | 5.8 | 6.5 |
| Adelphi | 5.5 | 4.2 | 3.9 | 5.5 | 6.2 |
| Baron | 5.8 | 4.7 | 4.5 | 5.5 | 6.1 |
| Birka | 6.0 | 4.9 | 4.4 | 5.7 | 5.6 |
| Cheri | 5.7 | 4.4 | 4.7 | 5.3 | 5.7 |
| Eclipse | 5.6 | 5.1 | 4.6 | 5.2 | 7.4 |
| Fylking | 4.7 | 3.2 | 4.7 | 5.3 | 5.9 |
| Glade | 5.8 | 4.9 | 3.9 | 5.7 | 6.7 |
| Kenblue | 3.8 | 4.1 | 4.8 | 3.3 | 3.6 |
| Merion | 5.7 | 4.0 | 4.9 | 4.7 | 5.9 |
| Merit | 6.1 | 4.7 | 4.6 | 5.7 | 6.6 |
| Parade | 5.3 | 4.8 | 4.9 | 5.2 | 5.5 |
| Ram I | 5.5 | 3.3 | 4.4 | 5.3 | 6.1 |
| S.D. Common | 2.7 | 3.7 | 5.1 | 3.5 | 3.0 |
| Sydsport | 6.0 | 4.7 | 4.8 | 5.3 | 5.5 |
| Touchdown | 5.1 | 4.3 | 4.8 | 4.7 | 6.5 |
| Vantage | 4.4 | 1.0 | 4.3 | 5.0 | 3.5 |
| LSD (.05) | 0.6 | 1.3 | 0.9 | 0.8 | 0.9 |

TABLE 11-continued

Turf quality of Ba 61-91 and other bluegrass varieties.

| | Turf Quality Rating* | | | | |
|---|---|---|---|---|---|
| Variety | Kingston, RI | Beltsville, MD | Blacksburg, VA | Blackstone, VA | Blackburg, VA |
| Ba 61-91 | 5.9 | 6.6 | 5.2 | 5.5 | 5.6 |
| Adelphi | 5.2 | 5.9 | 5.3 | 4.9 | 5.5 |
| Baron | 4.9 | 5.3 | 4.9 | 5.3 | 5.1 |
| Birka | 5.4 | 5.2 | 4.3 | 4.6 | 5.3 |
| Cheri | 5.2 | 5.1 | 5.1 | 5.1 | 5.0 |
| Eclipse | 5.8 | 5.9 | 5.8 | 6.2 | 5.1 |
| Fylking | 4.6 | 4.9 | 4.0 | 4.7 | 4.4 |
| Glade | 5.1 | 5.3 | 4.8 | 4.6 | 4.8 |
| Kenblue | 4.2 | 4.9 | 3.9 | 4.2 | 3.8 |
| Merion | 5.7 | 5.3 | 5.0 | 4.3 | 4.3 |
| Merit | 5.3 | 6.1 | 5.2 | 5.1 | 5.6 |
| Parade | 5.4 | 5.0 | 4.6 | 4.4 | 4.7 |
| Ram I | 5.3 | 4.6 | 4.4 | 4.8 | 4.4 |
| S.D. Common | 4.6 | 5.0 | 4.1 | 4.2 | 3.7 |
| Sydsport | 5.8 | 5.8 | 4.7 | 5.3 | 4.8 |
| Touchdown | 4.9 | 5.8 | 4.5 | 4.8 | 4.3 |
| Vantage | 5.1 | 5.5 | 4.6 | 3.8 | 4.5 |
| LSD (.05) | 0.9 | 0.8 | 0.7 | 0.8 | 0.9 |

*Rating Scale: 1-9,9 = ideal turf

TABLE 12

Mean turfgrass quality at thirty-two locations in National Bluegrass Evaluation Test of Ba 61-91 and other bluegrass varieties.

| Variety | Mean Turfgrass Quality Ratings* |
|---|---|
| Ba 61-91 | 5.3 |
| Adelphi | 5.2 |
| America | 5.1 |
| Baron | 5.2 |
| Birka | 5.2 |
| Cheri | 5.2 |
| Fylking | 4.9 |
| Glade | 5.3 |
| Kenblue | 4.2 |
| Merion | 5.1 |
| Merit | 5.3 |
| Nugget | 4.8 |
| Parade | 5.1 |
| Ram I | 5.2 |
| S.D. Common | 4.2 |
| Sydsport | 5.2 |
| Touchdown | 5.1 |
| Vantage | 4.6 |
| Wabash | 4.9 |
| LSD (.05) | .16 |

*Rating Scale: 1-9, 9 = ideal turf

TABLE 13

Mean turf quality of Ba 61-91 and other bluegrass varieties.

| | Mean Turf Quality Ratings* | | | | | |
|---|---|---|---|---|---|---|
| Variety | Mt. Carmel, CT | New Brunswick, NJ | Kingston, RI | Fairland, MD | Wye Mills, MD | Burlingham, VI |
| Ba 61-91 | 5.4 | 5.6 | 6.5 | 6.1 | 6.4 | 7.6 |
| Adelphi | 5.5 | 6.6 | 6.6 | 6.8 | 6.2 | 7.3 |
| Baron | 5.5 | 5.4 | 6.6 | 6.1 | 6.1 | 7.3 |
| Bonnieblue | 5.4 | 6.6 | 6.0 | 6.1 | 3.8 | 7.2 |
| Fylking | 5.7 | 5.5 | 6.4 | 6.2 | 3.6 | 7.0 |
| Glade | 5.8 | 6.6 | 6.2 | 6.1 | 5.1 | 7.0 |
| Kenblue | 5.7 | 3.2 | 5.0 | 5.5 | 5.3 | 6.1 |
| Merion | 5.3 | 5.8 | 6.6 | 5.8 | 5.6 | 8.0 |
| Parade | 5.7 | 6.4 | 6.5 | 6.5 | 6.3 | 6.9 |
| Park | 5.8 | 2.9 | 5.3 | 5.4 | 4.9 | 5.5 |
| Vantage | 5.7 | 5.6 | 6.1 | 6.5 | 6.2 | 7.3 |

| | Mean Turf Quality Ratings* | | | | | |
|---|---|---|---|---|---|---|
| Variety | Ithaca, NY | Blacksburg, VA | Newport News, VA | Beltsville, MD(1) | Beltsville, MD(2) | Mean |
| Ba 61-91 | 6.7 | 5.6 | 4.1 | 6.7 | 6.0 | |

TABLE 13-continued

Mean turf quality of Ba 61-91 and other bluegrass varieties.

| | | | | | | |
|---|---|---|---|---|---|---|
| Adelphi | 6.3 | 5.9 | 5.4 | 6.8 | 6.3 | 6.5 a–c |
| Baron | 6.4 | 5.3 | 5.1 | 6.0 | 6.4 | 6.1 g–r |
| Bonnieblue | 6.2 | 5.6 | 5.6 | 6.4 | 6.0 | 5.9 k–p |
| Fylking | 6.6 | 4.9 | 4.4 | 6.4 | 5.4 | 5.8 n–o |
| Glade | 6.4 | 5.3 | 5.4 | 6.2 | 5.7 | 6.0 i–n |
| Kenblue | 5.4 | 5.4 | 5.1 | 5.2 | 4.6 | 5.1 t–u |
| Merion | 6.6 | 5.5 | 6.3 | 6.7 | 5.9 | 6.2 e–k |
| Parade | 6.3 | 4.8 | 3.5 | 6.7 | 6.0 | 6.2 e–k |
| Park | 5.4 | 5.0 | 4.9 | 5.2 | 4.8 | 5.1 t–u |
| Vantage | 7.1 | 5.5 | 5.9 | 6.4 | 5.9 | 6.2 f–i |

*Rating Scale: 1–9, 9 = ideal turf

Means followed by the same letter are not significantly different according to Duncan's Multiple Range Test (p = 0.05).

(1) Moderate maintenance (2) Low maintenance

Two additional characteristics of Ba 61-91 make this grass economically signficant. Table 14 indicates the high sod strength of Ba 61-91 in comparison to other varieties of bluegrass. High sod strength is required in the cutting, removal and installation of sod to increase the efficiency of these operations. Table 15 indicates the high seed yield capacity of Ba 61-91 in comparison to Victa and Merit which are known to be high seed yielding varieties, and to Vantage and Windsor which are known to have significantly lower seed yielding capacity. High seed yielding capacity is required for economical seed production. Table 15 also indicates heading and anthesis dates of Ba 61-91 in comparison to other varieties. These two characteristics, in addition to the morphological characteristics noted in Table 1 and seed size and count per pound in Table 16, afford further bases for distinguishing Ba 61-91 from other varieties of Kentucky bluegrass.

TABLE 14

Sod strength of Ba 61-91 and other bluegrass varieties at Blacksburg, Virginia.

| Variety | Sod Strength Ratings* |
|---|---|
| Ba 61-91 | 5.3 a–h |
| Adelphi | 3.7 c–j |
| Baron | 3.7 c–j |
| Enmundi | 5.3 a–h |
| Glade | 5.0 a–i |
| Kenblue | 1.3 i–j |
| Merion | 1.7 h–j |
| Parade | 4.0 b–j |
| Park | 1.0 j |
| Sodco | 3.3 d–j |
| Sydsport | 4.0 b–j |

TABLE 14-continued

Sod strength of Ba 61-91 and other bluegrass varieties at Blacksburg, Virginia.

| Variety | Sod Strength Ratings* |
|---|---|
| Vantage | 1.7 h–j |

Means followed by the same letter are not significantly different according to Duncan's Multiple Range Test (probability = 0.05).

*Rating Scale: 9 = maximum sod strength

TABLE 15

Heading and anthesis date, seed yield per plant, and bushel weight of Ba 61-91 and other bluegrass varieties at Salem, Oregon.

| | Heading Date | | | | Anthesis Date | | | |
|---|---|---|---|---|---|---|---|---|
| | 1% | | 50% | | 1% | | 50% | |
| Variety | Year 1 | Year 2 | Year 1 | Year 2 | Year 1 | Year 2 | Year 1 | Year 2 |
| Ba 61-91 | 5/1 | 4/30 | 5/6 | 5/8 | 5/28 | 5/22 | 5/31 | 5/23 |
| Merit | — | 5/3 | — | 5/9 | — | 5/21 | — | 5/23 |
| Vantage | 4/12 | 4/21 | 4/22 | 4/24 | 5/17 | 5/19 | 5/24 | 5/20 |
| Victa | 5/3 | 5/8 | 5/6 | 5/12 | 5/24 | 5/21 | 5/27 | 5/23 |
| Windsor | 4/19 | 4/23 | 4/29 | 5/7 | 5/22 | 5/19 | 5/27 | 5/23 |

| | Seed Yield per Plant (gm) | | | Bushel Wt. (lb./bu.) |
|---|---|---|---|---|
| Variety | Year 1 | Year 2 | Year 3 | Year 3 |
| Ba 61-91 | 16 | 38.6 | 42.5 | 25.5 |
| Merit | — | — | 61.1 | 25.5 |
| Vantage | 8 | 11.4 | 4.8 | 18.5 |
| Victa | 38 | 57.6 | 45.4 | 25.0 |
| Windsor | 11 | 5.1 | 2.7 | 27.5 |

TABLE 16

Seed length and number of seeds per pound of Ba 61-91 and other bluegrass varieties.

| Variety | Seed Length (mm) | No. Seeds per Pound |
|---|---|---|
| Ba 61-91 | 2.85 | 1,075,331 |
| Baron | 2.72 | 1,181,474 |
| Fylking | 2.99 | 1,091,716 |
| Kenblue | 2.26 | 2,297,030 |
| Merion | 2.43 | 1,968,636 |
| Newport | 2.76 | 1,244,559 |
| Nugget | 3.31 | 873,942 |
| Park | 2.91 | 1,311,452 |
| Sydsport | 2.46 | 1,964,088 |
| Vantage | 2.51 | 1,555,848 |
| Victa | 2.95 | 1,053,867 |
| Windsor | 2.34 | 1,955,323 |

What is claimed and desired to be secured by Letters Patent is:

1. A variety of Kentucky bluegrass plant, substantially as shown and described, characterized particularly by a high level of resistance to diseases, a desirable dark green color throughout the growing season, a high quality and persistent turf under a wide range of environmental conditions and a high seed yielding capacity.

* * * * *